United States Patent [19]
Dantzig et al.

[11] Patent Number: 5,710,018
[45] Date of Patent: Jan. 20, 1998

[54] MAMMALIAN INFLUX PEPTIDE TRANSPORTER

[75] Inventors: Anne H. Dantzig, Crawfordsville; Jo Ann Hoskins, Indianapolis; Paul L. Skatrud, Greenwood, all of Ind.

[73] Assignee: Eli Lilly and Company, Indianapolis, Ind.

[21] Appl. No.: 463,345

[22] Filed: Jun. 5, 1995

Related U.S. Application Data

[62] Division of Ser. No. 13,462, Feb. 4, 1993, abandoned.
[51] Int. Cl.$^6$ .................................................. C12D 21/06
[52] U.S. Cl. .................. 435/69.1; 536/23.5; 435/240.2; 435/252.3; 435/320.1
[58] Field of Search .................. 536/23.5; 435/252.3, 435/252.33, 254.21, 254.23, 254.3, 320.1, 240.2, 172.3, 70.3, 71.1, 71.2, 69.1, 70.1

[56] References Cited

PUBLICATIONS

Saito, H. et al., Am. J. Physiol. 265:G289–G294 (1993).
Muller, U. et al., FASEB J. 8(N7):A1388 (1994).
Dantzig and Bergin, 1990, Biochimica et Biophysica Acta 1027:211–217.
Dantzig et al., 1992, Biochimica et Biophysica Acta 1112:167–173.
Kramer et al., 1990, Biochimica et Biophysica Acta 1030:41–49.
Kramer et al., 1990, Biochimica et Biophysica Acta 1030:50–59.
Ganapathy and Leibach, 1991, Current Opinion in Cell Biology 3:695–701.
Kramer et al., 1991, International Congress of Chemptherapy, Berlin, F.R.G. Abstract No. 1415.
Bird and Lloyd, 1990, Biochimica et Biophysica Acta 1024:267–270.
Skopicki, et al., 1991, Am. J. Physiol. 261:F670–F678.
Ganapathy, et al., 1981, J. Biol. Chem. 256:118–124.
Said, et al., 1988, Biochim. Biophys. Acta 941:232–240.
Kramer, et al., 1988, Biochim. Biophys. Acta 939:167–172.
Calonge, et al., 1990, Am. J. Physiol. 259:G775–G780.
Shimada and Hoshi, 1986, Jpn. J. Physiol. 36:451–465.
Matthews and Burston, 1984, Clinical Sci. 67:541–549.
Okano, et al., 1986, J. Biol. Chem. 261:14130–14134.
Nakashima, et al., 1984, Biochem. Pharm. 33:3345–3352.
Muranushi, et al., 1989, Pharm. Res. 6:308–312.
Friedman and Amidon, 1989, Pharm. Res. 6:1043–1047.
Friedman and Amidon, 1990, J. Control. Rel. 13:141–146.
Tabas, et al., 1991, 31st Interscience Conference on Antimicrobial Agents and Chemotherapy Abstract No. 164.
Dantzig, et al., 1992, 32nd Interscience Conference on Antimicrobial Agents and Chemotherapy, Anaheim, CA, Abstract No. 1460.
Snyder, et al., 1992, 32nd Interscience Conference on Antimicrobial Agents and Chemotherapy Abstract No. 1461.
Hoshi, 1986, Ion Gradient–Coupled Transport, INSERM Symposium No. 26. Editors: F. Alvarado and C. van Os, Elsevier Science Publishers.
Ganapathy and Leibach, 1983, J. Biol. Chem. 258:14189–14192.
Inui, et al., 1992, J. Pharmacol. Exp. Thera. 260:482–486.
Sezaki and Kimura, 1983, Topics in Pharmaceutical Sciences 133–142.
Okano, et al., 1986, Biochem. Pharmacol. 35:1781–1786.
Bai, et al., 1991, Pharm. Res. 8:593–599.
Kramer, 1987, Biochim. Biophys. Acta 905:65–74.
Miyamoto, et al., 1991, J. Biological Chemistry 266(8):4742–4745.
Kramer, et al., 1988, Biochem. Pharmacol. 37:2427–2435.
Asano et al., 1989, J. Biol. Chem. 264:3416–3420.
Reismeier et al., 1992, EMBO J. 13:4705–4713.
Kartner et al., 1991, Cell 64: 681–691.
Parkinson et al., 1990, J. Biol. Chem. 265: 12602–12610.
Liang et al., 1995, J. Biol. Chem. 270: 6456–6463.
Boll, et al., 1994, Pfleugers Arch. 429(1): 146–149.
Levinson, 1990, Meth. Enz. 185: 485–487.
Gold, 1990, Meth. Enz. 185: 11–14.
De Boer and Hui, 1990, Meth. Enz. 185: 103–114.
Balbas and Bolivar, 1990, Meth. Enz. 185: 14–37.
Uhlen and Moks, 1990, Meth Enz. 185: 129–143.
Kohno et al., 1990, Meth. Enz. 185: 187–195.
Han et al., 1992 Korean J. Biochem. 24: 123–130.
Grinnell et al., 1986, Mol. Cell. Biol. 6: 3596–3605.
Forman and Samuels, 1991, Gene 105: 9–15.
Hediger et al., 1989, Nature 330: 379–381.

*Primary Examiner*—Robert A. Wax
*Assistant Examiner*—Thomas W. MacAllister
*Attorney, Agent, or Firm*—Thomas D. Webster; Thomas G. Plant

[57] ABSTRACT

The present invention provides isolated DNA compounds and recombinant DNA vectors that encode mammalian influx peptide transporter activity. The invention also provides host cells transformed with these vectors and a method for production of mammalian influx peptide transporter activity by recombinant DNA techniques. The invention also provides a method for identifying compounds that are transported into the cell by the influx peptide transporter.

36 Claims, 2 Drawing Sheets

Plasmid pPSJ179

Plasmid pPSJ189

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 832 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 1:

```
Met  Ile  Leu  Gln  Ala  His  Leu  His  Ser  Leu  Cys  Leu  Leu  Met  Leu
1                   5                        10                       15

Tyr  Leu  Ala  Thr  Gly  Tyr  Gly  Gln  Glu  Gly  Lys  Phe  Ser  Gly  Pro
                    20                       25                       30

Leu  Lys  Pro  Met  Thr  Phe  Ser  Ile  Tyr  Glu  Gly  Gln  Glu  Pro  Ser
                    35                       40                       45

Gln  Ile  Ile  Phe  Gln  Phe  Lys  Ala  Asn  Pro  Pro  Ala  Val  Thr  Phe
                    50                       55                       60

Glu  Leu  Thr  Gly  Glu  Thr  Asp  Asn  Ile  Phe  Val  Ile  Glu  Arg  Glu
                    65                       70                       75

Gly  Leu  Leu  Tyr  Tyr  Asn  Arg  Ala  Leu  Asp  Arg  Glu  Thr  Arg  Ser
                    80                       85                       90

Thr  His  Asn  Leu  Gln  Val  Ala  Ala  Leu  Asp  Ala  Asn  Gly  Ile  Ile
                    95                       100                      105

Val  Glu  Gly  Pro  Val  Pro  Ile  Thr  Ile  Glu  Val  Lys  Asp  Ile  Asn
                    110                      115                      120

Asp  Asn  Arg  Pro  Thr  Phe  Leu  Gln  Ser  Lys  Tyr  Glu  Gly  Ser  Val
                    125                      130                      135

Arg  Gln  Asn  Ser  Arg  Pro  Gly  Lys  Pro  Phe  Leu  Tyr  Val  Asn  Ala
                    140                      145                      150
```

```
Thr Asp Leu Asp Asp Pro Ala Thr Pro Asn Gly Gln Leu Tyr Tyr
            155             160                     165
Gln Ile Val Ile Gln Leu Pro Met Ile Asn Asn Val Met Tyr Phe
            170             175                     180
Gln Ile Asn Asn Lys Thr Gly Ala Ile Ser Leu Thr Arg Glu Gly
            185             190                     195
Ser Gln Glu Leu Asn Pro Ala Lys Asn Pro Ser Tyr Asn Leu Val
            200             205                     210
Ile Ser Val Lys Asp Met Gly Gly Gln Ser Glu Asn Ser Phe Ser
            215             220                     225
Asp Thr Thr Ser Val Asp Ile Ile Val Thr Glu Asn Ile Trp Lys
            230             235                     240
Ala Pro Lys Pro Val Glu Met Val Glu Asn Ser Thr Asp Pro His
            245             250                     255
Pro Ile Lys Ile Thr Gln Val Arg Trp Asn Asp Pro Gly Ala Gln
            260             265                     270
Tyr Ser Leu Val Asp Lys Glu Lys Leu Pro Arg Phe Pro Phe Ser
            275             280                     285
Ile Asp Gln Glu Gly Asp Ile Tyr Val Thr Gln Pro Leu Asp Arg
            290             295                     300
Glu Glu Lys Asp Ala Tyr Val Phe Tyr Ala Val Ala Lys Asp Glu
            305             310                     315
Tyr Gly Lys Pro Leu Ser Tyr Pro Leu Glu Ile His Val Lys Val
            320             325                     330
Lys Asp Ile Asn Asp Asn Pro Pro Thr Cys Pro Ser Pro Val Thr
            335             340                     345
Val Phe Glu Val Gln Glu Asn Glu Arg Leu Gly Asn Ser Ile Gly
            350             355                     360
Thr Leu Thr Ala His Asp Arg Asp Glu Glu Asn Thr Ala Asn Ser
            365             370                     375
Phe Leu Asn Tyr Arg Ile Val Glu Gln Thr Pro Lys Leu Pro Met
            380             385                     390
Asp Gly Leu Phe Leu Ile Gln Thr Tyr Ala Gly Met Leu Gln Leu
            395             400                     405
Ala Lys Gln Ser Leu Lys Lys Gln Asp Thr Pro Gln Tyr Asn Leu
            410             415                     420
Thr Ile Glu Val Ser Asp Lys Asp Phe Lys Thr Leu Cys Phe Val
            425             430                     435
Gln Ile Asn Val Ile Asp Ile Asn Asp Gln Ile Pro Ile Phe Glu
            440             445                     450
Lys Ser Asp Tyr Gly Asn Leu Thr Leu Ala Glu Asp Thr Asn Ile
            455             460                     465
Gly Ser Thr Ile Leu Thr Ile Gln Ala Thr Asp Ala Asp Glu Pro
            470             475                     480
Phe Thr Gly Ser Ser Lys Ile Leu Tyr His Ile Ile Lys Gly Asp
            485             490                     495
Ser Glu Gly Arg Leu Gly Val Asp Thr Asp Pro His Thr Asn Thr
            500             505                     510
Gly Tyr Val Ile Ile Lys Lys Pro Leu Asp Phe Glu Thr Ala Ala
            515             520                     525
Val Ser Asn Ile Val Phe Lys Ala Glu Asn Pro Glu Pro Leu Val
            530             535                     540
Phe Gly Val Lys Tyr Asn Ala Ser Ser Phe Ala Lys Phe Thr Leu
```

|   |   |   |   | 545 |   |   |   | 550 |   |   |   | 555 |
|---|---|---|---|---|---|---|---|---|---|---|---|---|

Ile Val Thr Asp Val Asn Glu Ala Pro Gln Phe Ser Gln His Val
                                560                565                570

Phe Gln Ala Lys Val Ser Glu Asp Val Ala Ile Gly Thr Lys Val
                575                580                585

Gly Asn Val Thr Ala Lys Asp Pro Glu Gly Leu Asp Ile Ser Tyr
                590                595                600

Ser Leu Arg Gly Asp Thr Arg Gly Trp Leu Lys Ile Asp His Val
                605                610                615

Thr Gly Glu Ile Phe Ser Val Ala Pro Leu Asp Arg Glu Ala Gly
                620                625                630

Ser Pro Tyr Arg Val Gln Val Val Ala Thr Glu Val Gly Gly Ser
                635                640                645

Ser Leu Ser Ser Val Ser Glu Phe His Leu Ile Leu Met Asp Val
                650                655                660

Asn Asp Asn Pro Pro Arg Leu Ala Lys Asp Tyr Thr Gly Leu Phe
                665                670                675

Phe Cys His Pro Leu Ser Ala Pro Gly Ser Leu Ile Phe Glu Ala
                680                685                690

Thr Asp Asp Asp Gln His Leu Phe Arg Gly Pro His Phe Thr Phe
                695                700                705

Ser Leu Gly Ser Gly Ser Leu Gln Asn Asp Trp Glu Val Ser Lys
                710                715                720

Ile Asn Gly Thr His Ala Arg Leu Ser Thr Arg His Thr Asp Phe
                725                730                735

Glu Glu Arg Ala Tyr Val Val Leu Ile Arg Ile Asn Asp Gly Gly
                740                745                750

Arg Pro Pro Leu Glu Gly Ile Val Ser Leu Pro Val Thr Phe Cys
                755                760                765

Ser Cys Val Glu Gly Ser Cys Phe Arg Pro Ala Gly His Gln Thr
                770                775                780

Gly Ile Pro Thr Val Gly Met Ala Val Gly Ile Leu Leu Thr Thr
                785                790                795

Leu Leu Val Ile Gly Ile Ile Leu Ala Val Val Phe Ile Arg Ile
                800                805                810

Lys Lys Asp Lys Gly Lys Asp Asn Val Glu Ser Ala Gln Ala Ser
                815                820                825

Glu Val Lys Pro Leu Arg Ser
                830        832

(2) INFORMATION FOR SEQ ID NO:2:

(i) SEQUENCE CHARACTERISTICS:
        (A) LENGTH:2499 nucleotides
        (B) TYPE:nucleic acid
        (C) STRANDEDNESS:double
        (D) TOPOLOGY:linear (ii) MOLECULE TYPE:DNA (xi) SEQUENCE DESCRIPTION:SEQ ID NO:2:

```
ATGATACTTC AGGCCCATCT TCACTCCCTG TGTCTTCTTA TGCTTTATTT      50

GGCAACTGGA TATGGCCAAG AGGGGAAGTT TAGTGGACCC CTGAAACCCA     100

TGACATTTTC TATTTATGAA GGCCAAGAAC CGAGTCAAAT TATATTCCAG     150

TTTAAGGCCA ATCCTCCTGC TGTGACTTTT GAACTAACTG GGAGACAGA      200
```

-continued

| | | | | |
|---|---|---|---|---|
| CAACATATTT | GTGATAGAAC | GGGAGGGACT | TCTGTATTAC | AACAGAGCCT 250 |
| TGGACAGGGA | AACAAGATCT | ACTCACAATC | TCCAGGTTGC | AGCCCTGGAC 300 |
| GCTAATGGAA | TTATAGTGGA | GGGTCCAGTC | CCTATCACCA | TAGAAGTGAA 350 |
| GGACATCAAC | GACAATCGAC | CCACGTTTCT | CCAGTCAAAG | TACGAAGGCT 400 |
| CAGTAAGGCA | GAACTCTCGC | CCAGGAAAGC | CCTTCTTGTA | TGTCAATGCC 450 |
| ACAGACCTGG | ATGATCCGGC | CACTCCCAAT | GGCCAGCTTT | ATTACCAGAT 500 |
| TGTCATCCAG | CTTCCCATGA | TCAACAATGT | CATGTACTTT | CAGATCAACA 550 |
| ACAAAACGGG | AGCCATCTCT | CTTACCCGAG | AGGGATCTCA | GGAATTGAAT 600 |
| CCTGCTAAGA | ATCCTTCCTA | TAATCTGGTG | ATCTCAGTGA | AGGACATGGG 650 |
| AGGCCAGAGT | GAGAATTCCT | TCAGTGATAC | CACATCTGTG | GATATCATAG 700 |
| TGACAGAGAA | TATTTGGAAA | GCACCAAAAC | CTGTGGAGAT | GGTGGAAAAC 750 |
| TCAACTGATC | CTCACCCCAT | CAAAATCACT | CAGGTGCGGT | GGAATGATCC 800 |
| CGGTGCACAA | TATTCCTTAG | TTGACAAAGA | GAAGCTGCCA | AGATTCCCAT 850 |
| TTTCAATTGA | CCAGGAAGGA | GATATTTACG | TGACTCAGCC | CTTGGACCGA 900 |
| GAAGAAAAGG | ATGCATATGT | TTTTTATGCA | GTTGCAAAGG | ATGAGTACGG 950 |
| AAAACCACTT | TCATATCCGC | TGGAAATTCA | TGTAAAAGTT | AAAGATATTA 1000 |
| ATGATAATCC | ACCTACATGT | CCGTCACCAG | TAACCGTATT | TGAGGTCCAG 1050 |
| GAGAATGAAC | GACTGGGTAA | CAGTATCGGG | ACCCTTACTG | CACATGACAG 1100 |
| GGATGAAGAA | AATACTGCCA | ACAGTTTTCT | AAACTACAGG | ATTGTGGAGC 1150 |
| AAACTCCCAA | ACTTCCCATG | GATGGACTCT | TCCTAATCCA | AACCTATGCT 1200 |
| GGAATGTTAC | AGTTAGCTAA | ACAGTCCTTG | AAGAAGCAAG | ATACTCCTCA 1250 |
| GTACAACTTA | ACGATAGAGG | TGTCTGACAA | AGATTTCAAG | ACCCTTTGTT 1300 |
| TTGTGCAAAT | CAACGTTATT | GATATCAATG | ATCAGATCCC | CATCTTTGAA 1350 |
| AAATCAGATT | ATGGAAACCT | GACTCTTGCT | GAAGACACAA | ACATTGGGTC 1400 |
| CACCATCTTA | ACCATCCAGG | CCACTGATGC | TGATGAGCCA | TTTACTGGGA 1450 |
| GTTCTAAAAT | TCTGTATCAT | ATCATAAAGG | GAGACAGTGA | GGGACGCCTG 1500 |
| GGGGTTGACA | CAGATCCCCA | TACCAACACC | GGATATGTCA | TAATTAAAAA 1550 |
| GCCTCTTGAT | TTTGAAACAG | CAGCTGTTTC | CAACATTGTG | TTCAAAGCAG 1600 |
| AAAATCCTGA | GCCTCTAGTG | TTTGGTGTGA | AGTACAATGC | AAGTTCTTTT 1650 |
| GCCAAGTTCA | CGCTTATTGT | GACAGATGTG | AATGAAGCAC | TCAATTTTC 1700 |
| CCAACACGTA | TTCCAAGCGA | AAGTCAGTGA | GGATGTAGCT | ATAGGCACTA 1750 |
| AAGTGGGCAA | TGTGACTGCC | AAGGATCCAG | AAGGTCTGGA | CATAAGCTAT 1800 |
| TCACTGAGGG | GAGACACAAG | AGGTTGGCTT | AAAATTGACC | ACGTGACTGG 1850 |
| TGAGATCTTT | AGTGTGGCTC | CATTGGACAG | AGAAGCCGGA | AGTCCATATC 1900 |
| GGGTACAAGT | GGTGGCCACA | GAAGTAGGGG | GGTCTTCCTT | AAGCTCTGTG 1950 |
| TCAGAGTTCC | ACCTGATCCT | TATGGATGTG | AATGACAACC | CTCCCAGGCT 2000 |
| AGCCAAGGAC | TACACGGGCT | TGTTCTTCTG | CCATCCCCTC | AGTGCACCTG 2050 |
| GAAGTCTCAT | TTTCGAGGCT | ACTGATGATG | ATCAGCACTT | ATTTCGGGGT 2100 |
| CCCCATTTTA | CATTTTCCCT | CGGCAGTGGA | AGCTTACAAA | ACGACTGGGA 2150 |
| AGTTTCCAAA | ATCAATGGTA | CTCATGCCCG | ACTGTCTACC | AGGCACACAG 2200 |

| | | | | |
|---|---|---|---|---|
| ACTTTGAGGA | GAGGGCGTAT | GTCGTCTTGA | TCCGCATCAA | TGATGGGGGT 2250 |
| CGGCCACCCT | TGGAAGGCAT | TGTTTCTTTA | CCAGTTACAT | TCTGCAGTTG 2300 |
| TGTGGAAGGA | AGTTGTTTCC | GGCCAGCAGG | TCACCAGACT | GGGATACCCA 2350 |
| CTGTGGGCAT | GGCAGTTGGT | ATACTGCTGA | CCACCCTTCT | GGTGATTGGT 2400 |
| ATAATTTTAG | CAGTTGTGTT | TATCCGCATA | AAGAAGGATA | AAGGCAAAGA 2450 |
| TAATGTTGAA | AGTGCTCAAG | CATCTGAAGT | CAAACCTCTG | AGAAGCTGA 2499 |

MAMMALIAN INFLUX PEPTIDE TRANSPORTER

This application is a division of application Ser. No. 08/013,462 filed Feb. 4, 1993, now abandoned.

FIELD OF THE INVENTION

This invention relates to the field of recombinant deoxyribonucleic acid (hereinafter "DNA") technology. The invention provides isolated DNA compounds that comprise DNA encoding a proton-dependent influx peptide transport carrier (hereinafter "influx peptide transporter") activity. Recombinant DNA vectors and host cells are also provided.

BACKGROUND OF THE INVENTION

In mammalian cells, peptides are transported in and out of cells by several different transport carriers. Functionally, there are transporters responsible for the influx of peptides into the cell and transporters responsible for the efflux of peptides out of the cells. Influx transporters transport small peptides and related compounds into the cytoplasm, and are indirectly linked to an energy source through ion gradients. Efflux transporters consist of several different transporters that function to remove peptides from the cytoplasm. These include the P-glycoprotein that removes a number of oncolytics as well as hydrophobic peptides (Endicott and Ling, 1989, *Annu. Rev. Biochem.* 58:137–171; Sharma et al. 1992, *J. Biol. Chem.* 267:5731–5734).

The present invention relates to peptide transporters responsible for influx of peptides into cells or organelles. This class of peptide transporters is located in the gastrointestinal tract, kidney, placenta, and liver lysosomes (Ganapathy et al., 1991, *Indian J. Biochem. Biophys.* 28:317–323; Skopicki et al., 1991, *Am. J. Physiol.* 261:F670–F678; Ganapathy et al., 1981, *J. Biol. Chem.* 256:118–124; Bird and Lloyd, 1990, *Biochim. Biophys. Acta* 1024:267–270).

Generally, the influx peptide transporter is located in the brush border of the epithelial cells of the mucosa. Properties of the transporter have been studied in situ in intestinal mucosa preparations and in vitro with brush border membrane vesicles, isolated enterocytes, and cell culture. Studies have been conducted with preparations from the rat, hamster, rabbit, chicken, Japanese newt, and humans (Ganapathy and Leibach, 1991, *Curr. Biol.* 3:695–701; Said et al., 1988, *Biochim. Biophys. Acta* 941: 232–240; Kramer et al., 1988, *Biochim. Biophys. Acta* 939: 167–172; Colonge et al., 1990, *Am. J. Physiol.* 259:G775–G780; Shimada and Hoshi, 1986, *Jpn. J. Physiol.* 36: 451–465; Matthews and Burston, 1984, *Clinical Sci.*, 67:541–549). Many different solutes including small peptides (di- and tripeptides), antibiotics (including several oral β-lactams), oral angiotensin converting enzyme (ACE) inhibitors, and oral renin inhibitors are transported into the cytoplasm of the enterocyte by the influx peptide transporter (Ganapathy and Leibach, 1991, *Curr. Biol.* 3:695–701; Okano et al., 1986, *J. Biol. Chem.* 261:14130–14134; Nakashima et al., 1984, *Biochem. Pharm.* 33:3345–3352; Muranushi et al., 1989, *Pharm. Res.* 6:308–312; Friedman and Amidon, 1989, *Pharm. Res.* 6:1043–1047; Friedman and Amidon, 1990, *J. Control. Rel.* 13:141–146; Kramer, 1991, 17th International Congress of Chemotherapy, June 23–28, Berlin, F.R.G., Abstract No. 1415).

The influx peptide transporter plays a pivotal role in the absorption of certain oral drugs including β-lactam and ACE inhibitors. Out of 27 β-lactam antibiotics examined, the influx peptide transporter was able to distinguish between those that are orally absorbed in humans and those that are not (Tabas et al., 1991, 31st Interscience Conference on Antimicrobial Agents and Chemotherapy Abstract No. 164). Moreover, the influx peptide transporter has been demonstrated to transport a number of oral β-lactam antibiotics but not parenteral β-lactam antibiotics in studies using human intestinal Caco-2 cells and rabbit intestinal brush-border membranes (Dantzig et al., 1992, *Biochim. Biophys. Acta* 1112:167–173; Dantzig et al., 1992, 32nd Interscience Conference on Antimicrobial Agents and Chemotherapy, Anaheim, Calif., Abstract No. 1460; Snyder et al., 1992, 32nd Interscience Conference on Antimicrobial Agents and Chemotherapy Abstract No. 1461; Okano et al., 1986, *J. Biol. Chem.* 261:14130–14134.) Similar studies have been conducted to examine the ability of the influx peptide transporter to predict which ACE inhibitors are orally absorbed (Friedman and Amidon, 1989, *Pharm. Res.* 6:1043–1047).

The influx peptide transporter is sodium independent, energy dependent, cotransports protons with the substrate ("proton-dependent"), and exhibits the ability to concentrate the substrate to higher levels within the cell than is present outside the cell (Hoshi, 1986, *Ion Gradient-Coupled Transport*, INSERM symposium No. 26. Editors: F. Alvarado and C. H. van Os, Elsevier Science Publishers; Ganapathy and Leibach, 1991, *Curr. Opinion Cell Biol.* 3:695–701; Ganapathy et al., 1991, *Indian J. Biochem. Biophys.* 28:317–323). The substrate specificity of the influx peptide transporter has been examined in several species and appears to be quite similar if not identical (Inui et al., 1992, *J. Pharmacol. Exp. Thera.* 260:482–486; Ganapathy and Leibach, 1983, *J. Biol. Chem.* 258:14189–14192; Yasumoto and Sugiyama, 1980, *Agric. Biol. Chem.* 44:1339–1344; Nakashima et al., 1984, *Biochem. Pharmacol.* 33:3345–3352; Okano et al., 1986, *Biochem. Pharmacol.* 35:1781–1786). The binding site of the influx peptide transporter is not known and, consequently, absolute chemical structural features necessary for binding and transport of solutes are also unknown. Structural-activity relationship studies of substrates and inhibitors have been conducted to elucidate some of the structural features required for transport (Bai et al., 1991, *Pharm. Res.* 8:593–599; Snyder et al., 1992, 32nd Interscience Conference on Antimicrobial Agents and Chemotherapy, October 11–14, Anaheim, Calif., Abstract No. 1461).

Influx peptide transporter activity has been identified as a 127,000 dalton membrane protein from rabbit intestinal mucosa by photoaffinity labeling methods employing radiolabeled penicillin or a radiolabeled cephalexin analog (Kramer, 1987, *Biochim. Biophys. Acta* 905:65–74; Kramer et al., 1988, *Biochem. Pharmacol.* 37:247–2435). A purified 127,000 dalton protein from rabbit intestinal mucosa preparations reconstituted into liposomes resulted in binding and transport activities (Kramer et al., 1990, *Biochim. Biophys. Acta* 1030:50–59). The rabbit influx peptide transporter has been functionally expressed in *Xenopus laevis* oocytes (Miyamoto et al., 1991, *J. Biol. Chem.* 266:4742–4745). However, the structure of the cloned gene encoding the mammalian influx peptide transporter, or any component of it, has not been reported for any species.

Cloning of the influx peptide transporter would be useful for development of a method permitting the rapid identification and development of orally absorbed drugs that use this mechanism. Oral bioavailability is a highly desired property of many medications. Determination of the oral bioavailability of a drug at an early stage of development would be particularly advantageous. Presently, drugs are initially evaluated for oral bioavailability in animal models. This process requires selection of only a few compounds whose synthesis must be scaled up to be evaluated in these models. If the compounds are not orally absorbed using these models, analogs of the compounds are often made in an effort to achieve oral bioavailability. This process is time consuming, laborious, and expensive. Further, there are many examples of compounds that are well absorbed in animal models but not absorbed by humans. Other methods for evaluation are needed to complement this traditional approach.

SUMMARY OF THE INVENTION

The invention provides, inter alia, isolated DNA compounds that comprise a DNA sequence encoding mammalian influx peptide transporter activity, recombinant DNA expression vectors encoding mammalian influx peptide transporter activity, and host cells transformed with these recombinant DNA expression vectors. These recombinant DNA expression vectors and host cells are useful in a method for expressing mammalian influx peptide transporter activity, said method comprising:

(1) transforming a host cell with a recombinant DNA expression vector that comprises:
  (a) a promoter and a translational activating sequence that functions in said host cell; and
  (b) a DNA sequence encoding mammalian influx peptide transporter activity positioned for the expression from said promoter and translational activating sequence;

(2) culturing said host cell transformed in step (1) under conditions suitable for expression of influx peptide transporter activity.

The ability to predict oral availability of drugs in humans at an early stage in the drug discovery process would be advantageous. To that end, the invention provides an analytical tool useful in predicting the oral availability of drug compounds in humans by the influx peptide transporter. Thus, one embodiment of the invention concerns a method for measuring uptake of a compound by a cell comprising:

a) contacting said compound with a cell that is transformed with a recombinant DNA expression vector which provides expression of mammalian influx peptide transporter activity; and b) assaying for transport of said compound into said cell.

These and other aspects of the present invention, such as the use of the DNA sequence of this invention as a hybridization probe, are more fully described and claimed below.

DEFINITIONS

Coding sequence—the sequence of DNA in the open reading frame of a gene that encodes the amino acid residue sequence of the protein expressed from the gene.

DHFR—dihydrofolate reductase gene.

Gene—a segment of DNA that comprises a promoter, translational activating sequence, coding sequence, and 3' regulatory sequences, positioned to drive expression of the gene product.

Influx peptide transporter activity—translocation of a substrate across a membrane that is dependent on the presence of an inwardly directed proton gradient. Functionally, activity may be determined by measuring the transport of a compound across the membrane in the absence or presence of an excess of a known substrate of the transporter (for example, small peptides (e.g., di- and tripeptides), antibiotics (e.g., cephalexin), oral angiotensin converting enzyme (ACE) inhibitors, and oral renin inhibitors) in the presence of an inwardly directed pH-gradient (i.e., more acidic outside than inside the cell or membrane vesicle).

Promoter—a DNA sequence that directs or initiates the transcription of DNA.

Recombinant DNA Expression Vector—any autonomously replicating or integrating DNA agent, including but not limited to plasmids, comprising a promoter and other regulatory sequences positioned to drive expression of a DNA segment that encodes a polypeptide or RNA.

Recombinant DNA sequence—any DNA sequence, excluding the host chromosome from which the DNA is derived, which comprises a DNA sequence which has been isolated, synthesized, or partially synthesized.

Restriction Fragment—any linear DNA molecule generated by the action of one or more restriction enzymes.

Translational activating sequence—a regulatory DNA sequence that, when transcribed into mRNA, promotes translation of mRNA into protein.

All nucleotide and amino acid abbreviations used in this disclosure are those accepted by the United States Patent and Trademark Office as set forth in 37 C.F.R. §1.822(b)(1992).

DESCRIPTION OF THE FIGURES

The restriction enzyme and function maps presented an the drawings are approximate representations of the recombinant DNA vectors discussed herein. The restriction site information is not exhaustive. There may be more restriction enzyme sites of a given type than are actually shown on the map.

DETAILED DESCRIPTION

Figure 1:
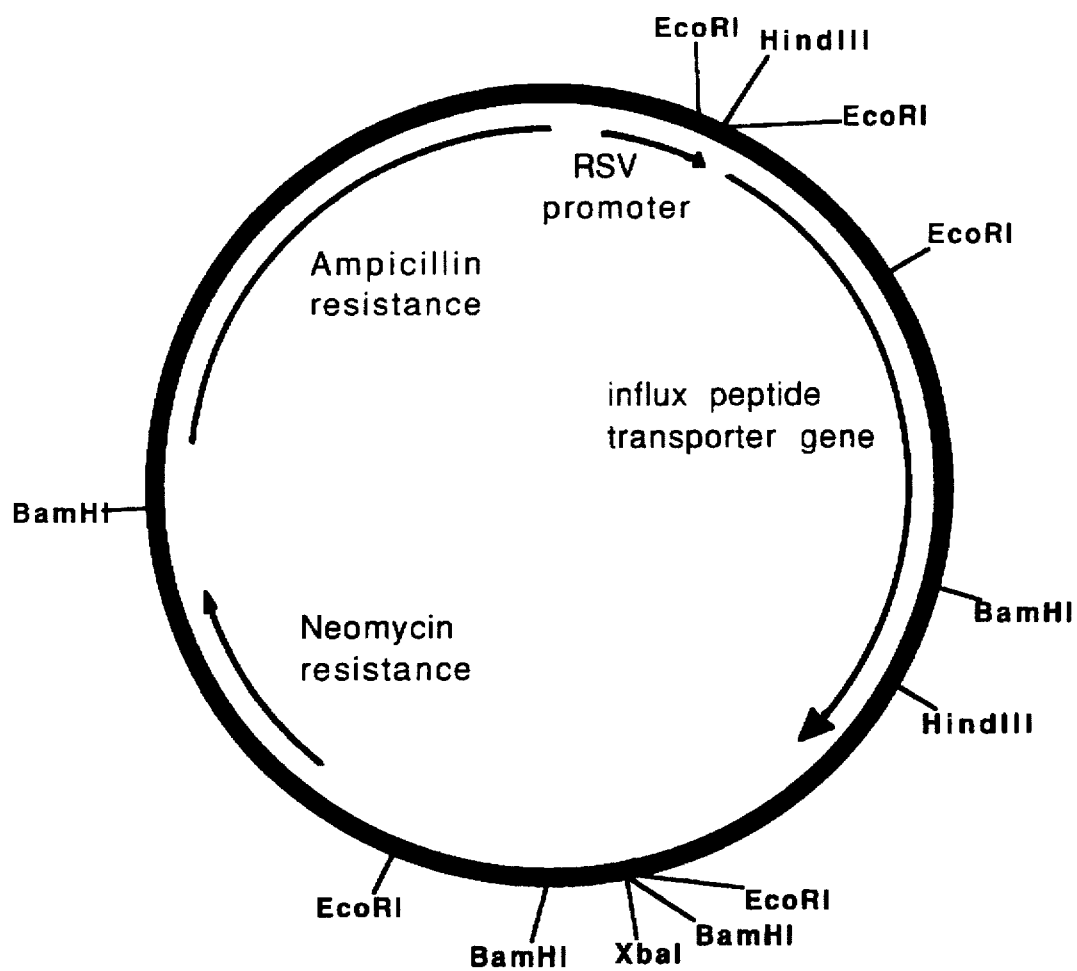
FIG. 1 is a restriction enzyme site and function map of plasmid pPSJ179.

The present invention provides isolated DNA compounds that comprise a DNA sequence encoding mammalian influx peptide transporter activity. The amino acid sequence of the influx peptide transporter is provided in the Sequence Listing as SEQ ID NO: 1. The DNA sequence encoding the influx peptide transporter is provided in the Sequence Listing as SEQ ID NO: 2.

Those skilled in the art will recognize that the degenerate nature of the genetic code enables one to construct many different DNA sequences that encode SEQ ID NO: 1. The DNA sequence depicted by SEQ ID NO: 2 is only one of many possible influx peptide transporter-encoding sequences. Consequently, the constructions described below and in the accompanying examples for the preferred DNA compounds, vectors, and transformants of the invention are merely illustrative and are not intended to limit the scope of the invention.

Now that the sequence of the influx peptide transporter is known, the sequence can be prepared by a variety of methods and, therefore, is not limited to any particular preparation means. The DNA sequences of the invention can be produced by a number of procedures, including DNA synthesis, cDNA cloning, genomic cloning, polymerase chain reaction (PCR) technology, or a combination of these approaches. These and other techniques are described by Maniatis, et al. *Molecular Cloning: A Laboratory Manual*, Cold spring Harbor Press, Cold Spring Harbor Laboratory, Cold Spring Harbor, N.Y. (1989), or *Current Protocols in Molecular Biology* (F. M. Ausbel et al., 1989). The contents of both of these references are incorporated herein by reference.

DNA sequences of the invention can be synthesized using commercially available methods and equipment. For example, the solid phase phosphotriester method can be used to produce the DNA sequences of this invention. The DNA sequences can be synthesized by the modified phosphotriester method using fully protected DNA building blocks. Such synthetic methods can be carried out in substantial accordance with the procedure of Itakura, et al., 1977, *Science* 198:1056 and Crea, et al., *Proc. Natl. Acad. Sci. U.S.A.* 75:575, and Narang, et al., 1980, *Methods in Enzymology* 68:90. In addition to manual procedures, the DNA sequences can be synthesized using automated synthesizers such as the ABS 380A DNA Synthesizer (Applied Biosystems, 850 Lincoln Centre Drive, Foster City, Calif. 94404). The DNA sequence can also be generated by the polymerase chain reaction. See, for example, U.S. Pat. Nos. 4,800,159 and 4,683,202, and European Patent Publication No. 0258017, published Mar. 2, 1987.

Methods for solution and solid phase synthesis are widely known, and various commercially available automatic synthesizers can be used in accordance with known protocols. See, for example, Stewart and Young, *Solid Phase Synthesis* 2d edition, Pierce Chemical Company, 1984; Tam et al., 1983, *J. Am. Chem. Assoc.* 105:6442; and Merrifield et al., 1982, *Biochemistry* 21:5020.

The DNA encoding mammalian influx peptide transporter activity can be cloned into a variety of vectors by means that are well known in the art. A number of suitable vectors may be used, including cosmids, plasmids, bacteriophage, baculoviruses and viruses. One of the principle requirements for such a vector is that it be capable of reproducing itself and transforming a host cell. Preferably, the vector will be a recombinant DNA expression vector that is capable of driving expression of the mammalian influx peptide transporter activity encoded by the DNA sequence of this invention. Typical expression vectors comprise a promoter region, a 5'-untranslated region, a coding sequence, a 3'-untranslated region, an origin of replication, a selective marker, and a transcription termination site. In addition, the vectors useful in the present invention may further comprise sequences that allow for replication in *Escherichia coli*, as it is usually more efficient to prepare plasmid DNA in *E. coli* than in other host organisms.

A wide variety of expression vectors exist that can be modified to express the novel DNA sequences of this invention. The specific vectors exemplified herein are merely illustrative, and are not intended to limit the scope of the invention. Expression methods are described by Maniatis, et al. *Molecular Cloning: A Laboratory Manual* or *Current Protocols in Molecular Biology* 16.3–17.44 (1989). Expression methods in Saccharomyces are also described in *Current Protocols in Molecular Biology* (1989).

Suitable vectors for use in practicing the invention include prokaryotic vectors such as the pNH vectors (Stratagene Inc., 11099 N. Torrey Pines Rd., LaJolla, Calif. 92037), pET vectors (Novogen Inc., 565 Science Dr., Madison Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); baculovirus vectors such as pVL1392, pVL1393, or pAC360 (Invitrogen); and yeast vectors such as YRP17, YIP5, and YEP24 (New England Biolabs, Beverly, Mass.), as well as pRS403 and pRS413 Stratagene Inc.) and Picchia vectors such as pHIL-D1 Phillips Petroleum Co., Bartlesville, Okla. 74004).

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, Adenovirus promoters, SV40 promoters, Rous Sarcoma Virus promoters, Cytomegalovirus promoters, baculovirus promoters such as AcMNPV polyhedrin promoter, Picchia promoters such as the alcohol oxidase promoter, and Saccharomyces promoters such as the gal4 inducible promoter and the PGK constitutive promoter.

In addition, a vector of this invention may contain any one of a number of various markers facilitating the selection of a transformed host cell. Such markers include genes associated with temperature sensitivity, drug resistance, or enzymes associated with phenotypic characteristics of the host organisms.

After the DNA sequence encoding mammalian influx peptide transporter activity has been inserted into the vector, the vector may be used to transform a host cell. In general, the host cell may comprise any cellular organism including a prokaryotic cell or eukaryotic cell that is capable of being transformed with the vector comprising the DNA of this invention. The techniques of transforming and transfecting cells are well known in the art and may be found in such general references as Maniatis, et al. (1989) or *Current Protocols in Molecular Biology* (1989).

The present invention is not limited in use to a particular host cell. The vectors of the invention can be transformed into and expressed in many host cells. Transformed host cells of this invention may be cultured in conventional nutrient media modified as appropriate for inducing promoters, selecting transformants or amplifying genes. The culture conditions, such as temperature, pH and the like, are those previously used with the host cell selected for expression, and will be apparent to the ordinarily skilled artisan.

The choice of a particular host cell depends to some extent on the particular expression vector used to drive expression of the influx peptide transporter activity-encoding DNA compounds of this invention. After transformation of a vector of the invention into a host cell one can select transformants on the basis of a selectable phenotype. This selectable phenotype can be conferred by a selectable marker present on the expression vector.

Suitable host cells include, for example, prokaryotic cells such as *Escherichia coli* and *Bacillus subtilis;* eukaryotic cells such as Chinese hamster ovary cells CHO-DHFR⁻ (available from the American Type Culture Collection (ATCC), 12301 Parklawn Drive, Rockville, Md. 20852-1776, under accession number ATCC CRL-9096), Chinese hamster ovary cells CHO-K1 (ATCC CCL-61), Syrian Hamster cells AV12 (ATCC CRL 1573), human lymphocyte CCRF-CEM cells, human neuroblastoma cells, pig kidney cells (LLC-PK$_1$, ATCC CL101), and cells derived from liver, brain, skin, and adrenal gland; yeast cells, including

*Saccharomyces cerevisiae* and *Picchia pastoris;* insect cells including army worm cells, such as *Spodoptera frugiperda* Sf9 (ATCC CRL 1711); and fungal cells including Aspergillus species.

Expression in prokaryotic and eukaryotic cells is described by Maniatis et al. (1989), and Kaufmann, *Genetic Engineering Principles and Methods,* ed. J. K. Setlow, Plenum Press 9:155, (1988). Yeast expression is described by Barr, et al., *Yeast Genetic Engineering,* eds. Butterworth, Boston 1989. Expression in insect cells is described by Maeda, 1989, *Annual Review of Entomology* 34:351.

The DNA sequence depicted by SEQ ID NO: 2 was derived from cDNA clones prepared from the mRNA of the Caco-2 cell line. The Caco-2 cell line is a human colon adenocarinoma cell line that has been shown to take up antibiotics by an influx peptide transporter (Dantzig and Bergin, 1990, *Biochim. Biophys. Acta* 1027:211–217; Dantzig et al., 1992, *Biochim. Biophys. Acta* 1112: 167–173). Caco-2 cells are available from the ATCC under accession number ATCC HTB37.

The illustrative vectors of the present invention were transformed into *Escherichia coli* RR1 or *E. coli* DH5α cells and deposited and made part of the permanent stock culture collection of the Northern Regional Research Laboratories (NRRL) in Peoria, Ill. 61604, on Jan. 21, 1993. The specific cultures and accession numbers are found in Table 1.

TABLE 1

| Culture | Accession Number |
| --- | --- |
| *E. coli* K12 DH5α/pPSJ179 | NRRL B-21041 |
| *E. coli* K12 RR1/pPSJ189 | NRRL B-21042 |

The cultures are obtained and the plasmids are isolated using conventional techniques. The plasmids then may be directly transformed into host cells for the production of the mammalian influx peptide transporter.

Plasmid pPSJ179 is approximately 8500 base pairs in length and contains DNA encoding the influx peptide transporter from Caco-2 cells. Plasmid pPSJ179 was constructed by cloning a 3.4 kb XbaI-HindIII cDNA restriction enzyme fragment that comprises the influx peptide transporter-encoding DNA into the commercially available vector pRc/RSV (Invitrogen). Because the influx peptide transporter has an internal HinIII restriction enzyme site, a partial restriction enzyme digestion was used in the cloning of the 3.4 kb XbaI-HindIII fragment. Plasmid pPSJ179 contains the ampicillin resistance gene for selection in *Escherichia coli,* neomycin resistance gene for selection in eukaryotic cells and the influx peptide transporter gene positioned for expression from the Rous Sarcoma virus (RSV) promoter. A restriction enzyme and function map of plasmid pPSJ179 is provided in FIG. 1 of the accompanying drawings.

Figure 2:
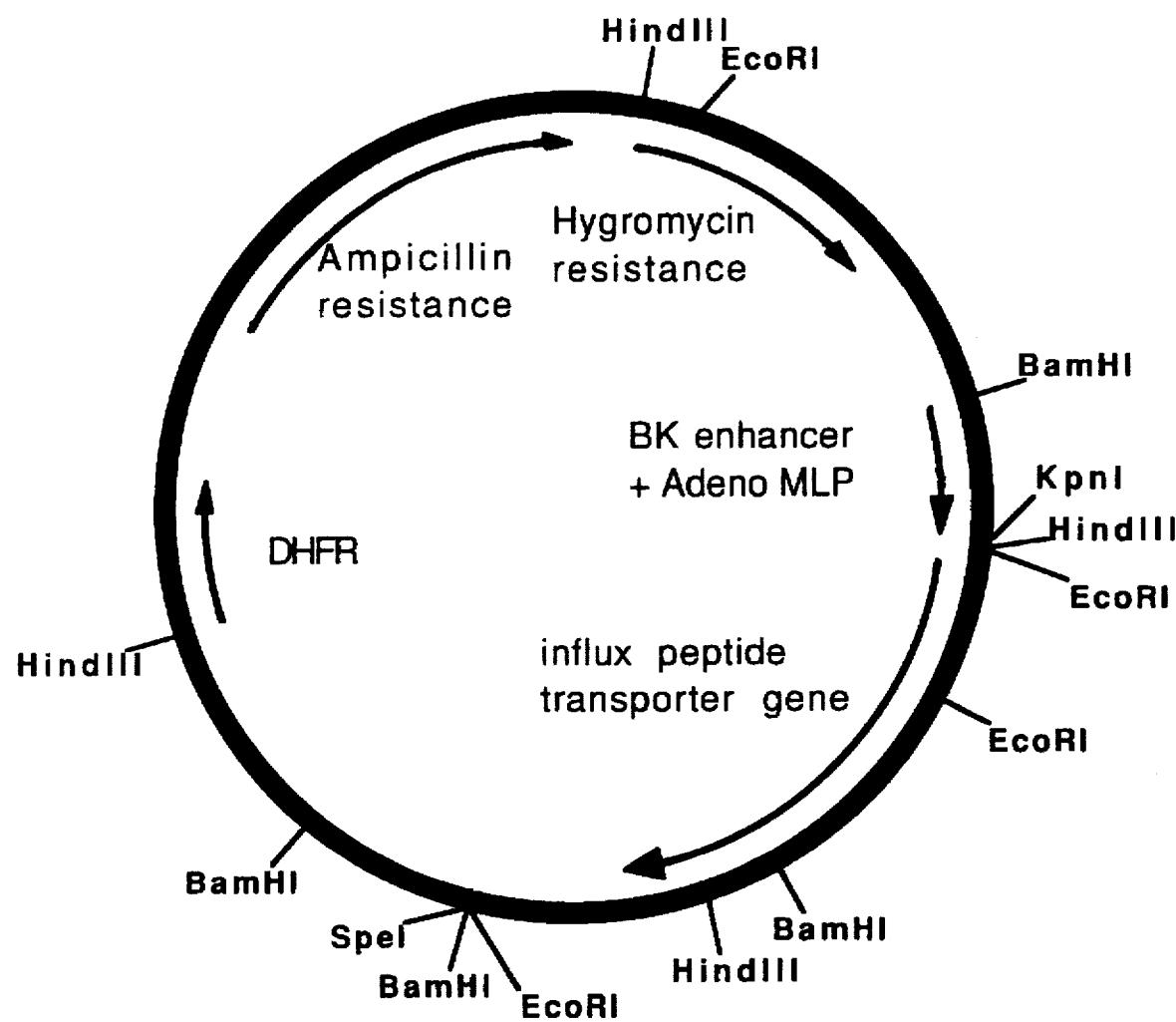
FIG. 2 is a restriction enzyme site and function map of plasmid pPSJ189.

Plasmid pPSJ189 is also illustrative of the vectors of the present invention. Plasmid pPSJ189 is approximately 12.2 kilobases in size. Plasmid pPSJ189 contains a 3.4 kilobase pair KpnI-SpeI restriction fragment containing the influx peptide transporter-encoding DNA cloned into a modified version of the plasmid pHD. The plasmid pHD was modified to contain restriction enzyme sites to facilitate the cloning of the 3.4 kilobase pair KpnI-SpeI restriction fragment containing the influx peptide transporter-encoding DNA. Plasmid pHD is described in European Patent Publication No. 0245949, published on Nov. 19, 1987. Plasmid pPSJ189 contains an ampicillin resistance gene for selection in *Escherichia coli,* hygromycin resistance gene for selection in eukaryotic cells, a DHFR gene, and the BK enhancer and Adenovirus Major Late Promoter positioned for expression of the influx peptide transporter gene. A restriction enzyme and function map of plasmid pPSJ189 is provided in FIG. 2 of the accompanying drawings.

The ordinarily skilled artisan will recognize that the influx peptide transporter-encoding DNA can be excised from plasmids pPSJ179 and pPSJ189 on a variety of restriction enzyme fragments and cloned into a great number of expression vectors. For example, the influx peptide transporter-encoding activity DNA can be excised from plasmid pPSJ179 on a 3.4 kilobase pair HindIII-XbaI restriction enzyme fragment or from the plasmid pPSJ189 on a 3.4 kilobase pair KpnI-SpeI restriction enzyme fragment. Because of the presence of multiple restriction enzyme sites within the plasmid DNA, the ordinarily skilled artisan will recognize that partial restriction enzyme digestions may be needed to produce a DNA fragment encoding the intact influx peptide transporter. Techniques for identifying, isolating and cloning various restriction enzyme fragments that comprise influx peptide transporter-encoding activity DNA are well known in the art.

Based on the present disclosure, other transporters similar in structure to the influx peptide transporter of this invention may be identified by well known techniques such as polymerase chain reaction (PCR) technology, DNA hybridization, or by a combination of these procedures. The influx peptide transporter is comprised of an extracellular region (approximately amino acid residues 1 to 778 of SEQ. ID. NO:1) and a transmembrane region (approximately amino acid residues 778 to 809 of SEQ. ID. NO:1). The extracellular region is highly related to the family of proteins known as the cadherins (Takeichi, M., 1990, *Annu. Rev. Biochem.* 59:237–252). The cadherin family possesses highly conserved extracellular and intracellular regions. However, the influx peptide transporter does not have the conserved intracellular region shown to be necessary for cadherin functional activity (Klinter, 1992, *Cell* 69:225–236). A hybridization strategy based on this difference between the cadherins and the influx peptide transporter can be used to identify proteins related to the influx peptide transporter.

Under one hybridization strategy, probes are generated that are specific to a) the conserved extracellular region of the cadherin family and influx peptide transporter, and b) the conserved intracellular region of the cadherin family. PCR technology can be used to generate such probes. In this case, template DNA can be either genomic DNA, or cDNA taken from cell lines of different tissue types that express influx transporter activity and cadherins. Potential sources for template DNA include cells from the kidney, intestinal tract, pancreas or endothelial cells from the "blood-brain" barrier.

Probes specific for the highly conserved extracellular region of the cadherin family and influx peptide transporter are first used in hybridization experiments to identify the genes that have the extracellular region of cadherins and other peptide transporters. Probes generated from the intracellular region of cadherins are then used as hybridization probes to identify those genes that encode cadherins. Those genes that react with the probe to the extracellular region, but not the intracellular region, represent candidate influx peptide transporters. These genes are cloned into recombinant DNA expression vectors and transformed into an appropriate host cell. The transformed host cell is then assayed for the expression of influx peptide transporter activity.

Heterologous hybridization procedures can be used to accomplish the same result. In this case DNA fragments representing the extracellular and intracellular portions of the cadherins are used to differentiate potential influx peptide transporters from the cadherins.

Traditional hybridization strategies that utilize probes based on the DNA encoding the influx peptide transporter of this invention, or any portion thereof, may be used to identify other genes encoding peptide transport activity. For example, probes based on SEQ ID. NO: 2, or a portion thereof, may be used to identify genes with peptide transport activity. Degenerate probes based on the amino acid sequence of SEQ ID. NO: 1, or a portion thereof, may also be used to identify genes with peptide transport activity. Hybridization techniques are described by Maniatis et al. (1989)

As indicated above, the present invention provides a method for measuring uptake of a compound by the influx peptide transporter. This method is useful in predicting the oral bioavailability of compounds by the influx peptide transporter in humans. A wide variety of compounds can be tested for uptake by the influx peptide transporter. Examples of such compounds include small peptides and therapeutic agents, such as antibiotics, ACE inhibitors and renin inhibitors. These compounds are merely illustrative. This method is applicable to virtually any compound to test its ability to be taken up by the influx peptide transporter. Thus, one embodiment of this invention provides a method for measuring uptake of a compound into a cell which comprises:

a) contacting said compound with a cell that is transformed with a recombinant DNA expression vector which provides expression of mammalian influx peptide transporter activity, and b) assaying for transport of said compound into said cell.

Illustrative recombinant DNA expression vectors which provide expression of influx peptide transporter activity that are useful in the method of this invention are described above. Such recombinant DNA expression vectors can be tailored for optimal expression of influx peptide transporter activity in the host cell that is chosen for expression.

A wide variety of cells, including those described above, may be used in this method. Cells that lack influx peptide transporter activity before transformation with a recombinant DNA expression vector of this invention are especially useful in the method. Also useful are cells that possess measurable uptake of a compound before transformation with a recombinant DNA expression vector of this invention. In either case, cells that are transformed with a recombinant DNA expression vector encoding influx peptide transporter activity can be assayed for increased transport of a test compound into the cell.

Cells that are useful in this aspect of the invention include, for example, prokaryotic cells such as *Escherichia coli* and *Bacillus subtilis;* eukaryotic cells such as Chinese hamster ovary cells CHO-DHFR⁻ (available from the American Type Culture Collection (ATCC), 12301 Parklawn Drive, Rockville, Md. 20852-1776, under accession number ATCC CRL-9096), Chinese hamster ovary cells CHO-K1 (ATCC CCL-61), Syrian Hamster cells AV12 (ATCC CRL 1573), human lymphocyte CCRF-CEM cells, human neuroblastoma cells, pig kidney cells (LLC-PK$_1$, ATCC CL101), and cells derived from liver, brain, skin, and adrenal gland; yeast cells, including *Saccharomyces cerevisiae* and *Picchia pastoris;* insect cells including army worm cells, such as *Spodoptera frugiperda* Sf9 (ATCC CRL 1711); and fungal cells including Aspergillus species. Peptide transport deficient mutants of the above-referenced cells will also be useful in the method of this invention. Such peptide transport deficient mutants have been described for *Escherichia coli* (DeFelice et al., 1973, *J. Bacteriol.* 116:751-7560), and yeast (Island et al., 1991, *Curr. Genet.* 20:457–463, Marder et al., 1978, *J. Bacteriol.* 136:1174–1177).

As noted above, the particular vector that is used to express the influx peptide transporter will vary depending on the host cell that is utilized.

Uptake of a compound by a transfectant cell expressing influx peptide transporter activity can be measured by a variety of methods. These methods include measurement of the appearance of the test compound within the host cell by lysing the cell and analyzing a sample of the lysate for the compound by high performance liquid chromatography or by detection of radioactive activity in the case where the compound is radiolabeled. Alternatively, other attributes associated with the particular test compound could be measured. Thus, assays commonly employed for screening a particular compound can be utilized. For example, the ability of the compound to displace (or enhance) the binding of a ligand to a receptor in a receptor assay, the ability of the compound to inhibit (or stimulate) an enzyme of interest, the ability of the compound to inhibit (or stimulate) the growth of an organism(s), or some other attribute that the test compound might possess. A variety of assays can be used to measure influx peptide transporter activity including those described by Bradner and Claridge, 1984, Screening Systems in *Antineoplastic Agents,* (eds. W. A. Remers, Wiley-Interscience Pub., John Wiley and Sons, Inc. N.Y., N.Y.).

The following Examples are intended to assist in the further understanding of the invention. Particular materials employed, species, and conditions are intended to be further illustrative of the invention and not limiting the reasonable scope thereof. Procedures for the manipulation and analysis of DNA were performed essentially as described by Maniatis, et al. (1989). Conditions for restriction enzyme reactions were those recommended by the manufacturers (Boehringer Mannheim (BM), Indianapolis, Ind.; New England Biolabs (NEB), Beverly, Mass.; Bethesda Research Labs (BRL), Gaithersburg, Md.).

EXAMPLE 1

Chinese hamster ovary cells (CHO-K1, ATCC CCL 61) were transfected with plasmid pPSJ179 using a calcium precipitation protocol described in the Stratagene mammalian transfection kit (Stratagene Catalog #200285). Plasmid pPSJ179 can be isolated from *Escherichia coli* K12 DH5α/ pPSJ179 (NRRL B-21041) using a standard alkaline-SDS procedure (Maniatis et al., 1989). The calcium precipitation protocol transfection method was carried out as follows. Subconfluent CHO-K1 cells (100 mm culture dish, 1-day post plating) were incubated for 20 minutes at 37° C. with 20 µg of a calcium-precipitated DNA sample. The DNA sample was either plasmid pPSJ179 or, as control, plasmid pRc/RSV. Subsequently, the cells were grown for 3 days in F12 medium containing 10% fetal bovine serum (Hyclone Laboratories Inc., Logan, Utah 84321). Afterwards, the medium was replaced with growth medium containing the selection agent, G-418 sulfate at 300 µg/ml (Gibco, Grand Island, N.Y.) and cells were grown in a 3% $CO_2$ incubator at 37° C. for 13 days. Colonies which were selected for further study were grown for selected time periods in the selection medium at 37° C. in a 5% $CO_2$ incubator. Transfectants were evaluated for expression of the influx peptide transporter using an enzyme linked immunosorbent assay (ELISA) and monoclonal antibody reactive with the influx peptide transporter. Clones that expressed higher levels of the influx peptide transporter antigen than the control were selected for transport studies. Alternatively, clones are selected for expression of the influx peptide transporter using the methods described by Dantzig et al., 1990, *Biochim. Biophys. Acta* 1027:211–217. Hybridization techniques utilizing probes based on SEQ. ID. NO: 1 may also be used to identify clones that contain DNA encoding the influx peptide transporter.

EXAMPLE 2

Clones selected in Example 1 were evaluated for the uptake of the antibiotic cephalexin. Cephalexin is available from Eli Lilly and Company, Indianapolis, Ind. The transfected CHO-K1 cells (~0.5 to 1×10⁵ cells per well) were grown for 3 days in a Costar 24-well plate as described above. Confluent cells were washed with Earle's balanced salt solution (Gibco, Grand Island, N.Y.) containing 25 mM HEPES, pH 7.4 (Trans-EBSS) and incubated 45 minutes at 37° C., and then the Trans-EBSS was removed by aspiration. The cells were incubated in the presence of 1 mM [$^{14}$C] cephalexin in sodium-free Earle's balanced salt solution containing 120 mM choline chloride, 25 mM MES, pH 6.0 (sodium-free, Trans-EBSS) at 37° C. for 2 hours. Subsequently, cells were washed with ice cold Trans-EBSS, pH 7.4, lysed in 0.2N NaOH, and an aliquot was removed for scintillation counting.

A representative transfectant (Clone 9) displayed significantly higher uptake of [$^{14}$C]cephalexin than the control. A further study indicated that uptake of 1 mM cephalexin by this transfectant was inhibited by the presence of 50 mM of Gly-L-Pro (GP), a dipeptide that competes for uptake by the influx peptide transporter. Coincubation of the cells with 1 mM [$^{14}$C] cephalexin and GP decreased drug uptake in the representative transfectant (Clone 9) to the level of the control cells. Moreover, transport of 1 mM [$^{14}$C]cephalexin by the control cells was not inhibited by the Gly-L-Pro dipeptide. The results of these studies are provided in Table 2.

TABLE 2

| Sample | $^{14}$C-Cephalexin Uptake (nmol/mg total cell protein) |
| --- | --- |
| Clone 9 | 6.6 ± 0.3 |
| Clone 9 + GP | 4.5 ± 0.03 |
| Control | 3.3 ± 0.6 |
| Control + GP | 4.7 ± 0.4 |

We claim:

1. An isolated DNA compound that comprises a DNA sequence encoding a protein with the amino acid residue sequence of SEQ ID NO:1.

2. An isolated DNA compound of claim 1 which comprises the DNA sequence of SEQ ID NO: 2.

3. A recombinant DNA vector that comprises the DNA sequence of claim 1.

4. A recombinant DNA vector of claim 3 that further comprises a promoter and translational activating sequence positioned to drive expression of said DNA sequence.

5. A recombinant DNA vector of claim 4 wherein said promoter functions in a eukaryotic cell.

6. A recombinant DNA vector of claim 4 wherein said promoter functions in a prokaryotic cell.

7. A host cell transformed with the recombinant DNA vector of claim 5.

8. A host cell transformed with the recombinant DNA vector of claim 6.

9. A host cell of claim 7 that is eukaryotic.

10. A host cell of claim 8 that is prokaryotic.

11. A host cell of claim 9 selected from the group consisting of mammalian cells, yeast cells, insect cells, and fungal cells.

12. A host cell of claim 11 selected from the group consisting of Chinese Hamster Ovary cells, Syrian Hamster AV12 cells, Saccharomyces cells, Pichia cells, army worm cells, and Aspergillus cells.

13. A host cell of claim 8 selected from the group consisting of *Escherichia coli* and *Bacillus subtilis*.

14. A recombinant DNA vector that comprises the DNA sequence of claim 2.

15. A recombinant DNA vector of claim 14 that further comprises a promoter and translational activating sequence positioned to drive expression of said DNA sequence.

16. A recombinant DNA vector of claim 15 wherein said promoter functions in a eukaryotic cell.

17. A recombinant DNA vector of claim 15 wherein said promoter functions in a prokaryotic cell.

18. A host cell transformed with the recombinant DNA vector of claim 16.

19. A host cell transformed with the recombinant DNA vector of claim 17.

20. A host cell of claim 18 that is eukaryotic.

21. A host cell of claim 19 that is prokaryotic.

22. A host cell of claim 20 selected from the group consisting of mammalian cells, yeast cells, insect cells, and fungal cells.

23. A host cell of claim 22 selected from the group consisting of Chinese Hamster Ovary cells, Syrian Hamster AV12 cells, Saccharomyces cells, Pichia cells, army worm cells, and Aspergillus cells.

24. A host cell of claim 21 selected from the group consisting of *Escherichia coli* and *Bacillus subtilis*.

25. The recombinant DNA vector of claim 14 that is plasmid pPSJ179.

26. The recombinant DNA vector of claim 14 that is plasmid pPSJ189.

27. A host cell transformed with the recombinant DNA vector of claim 25.

28. A host cell transformed with the recombinant DNA vector of claim 26.

29. The transformed host cell of claim 23 that is CHO-K1/pPSJ179.

30. The transformed host cell of claim 23 that is CHO-K1/pPSJ189.

31. A method of expressing influx peptide transporter activity, said method comprising;

(1) transforming a host cell with a recombinant DNA expression vector that comprises:
  (a) a promoter and a translational activating sequence that functions in said host cell; and
  (b) a DNA sequence encoding the mammalian influx peptide transporter of SEQ ID NO:1 positioned for the expression from said promoter and translational activating sequence;

(2) culturing said host cell transformed in step (1) under conditions suitable for expression of mammalian influx peptide transporter activity.

32. The method of claim 31 wherein said host cell is prokaryotic.

33. The method of claim 31 wherein said host cell is eukaryotic.

34. The method of claim 33 selected from the group consisting of mammalian cells, yeast cells, insect cells, and fungal cells.

35. The method of claim 34 selected from the group consisting of Chinese Hamster Ovary cells, Syrian Hamster AV12 cells, Saccharomyces cells, Pichia cells, army worm cells, and Aspergillus cells.

36. The method of claim 32 selected from the group consisting of Escherichia and *Bacillus subtilis*.

* * * * *